United States Patent [19]

Hilverda

[11] Patent Number: Plant 5,517

[45] Date of Patent: Jul. 16, 1985

[54] CARNATION NAMED HILSTAR

[75] Inventor: Jan J. Hilverda, Aalsmeer, Netherlands

[73] Assignee: Hilverda B.V., Aalsmeer, Netherlands

[21] Appl. No.: 559,359

[22] Filed: Dec. 8, 1983

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—Chas. W. Rummler

[57] ABSTRACT

A new variety of spray carnation having relatively small, bright red blooms which are produced continuously and profusely on sturdy, upright flower stems, the flowers being distinguished by their folded petals which are deeply and more serrated than usual, the plant itself having a vigorous and rapid growth rate reaching a height of about one meter.

1 Drawing Figure

BACKGROUND OF THE NEW PLANT

This new carnation variety was discovered by me in 1977 as a seedling of unknown parentage growing among a field of carnations maintained by me for breeding purposes at Aalsmeer, The Netherlands. This particular plant was selected for propagation and test because of its tall, sturdy growth habit and its profuse production of bright red flowers and my progressive propagation of this new plant, by cuttings, at Aalsmeer clearly demonstrated that the novel characteristics of this new plant would hold true from generation to generation and appeared to be firmly fixed.

DESCRIPTION OF THE DRAWING

My new variety of spray carnation is illustrated by the accompanying photographic drawing which shows, in full color, the upper portion of a typical spray stem bearing buds in various stages, as well as fully opened flowers, the view including a face view of a fully opened flower and parts of a half opened bud, the colors shown being as nearly true as it is reasonably possible to obtain by conventional photographic procedures.

DESCRIPTION OF THE NEW PLANT

The following is a detailed description of my new carnation plant based upon observations of greenhouse grown plants made at Aalsmeer, The Netherlands, in January 1983, the color designations being according to The R.H.S. Colour Chart published by The Royal Horticultural Society of London, England.

THE PLANT

Origin: Seedling.
Parentage: Unknown.
Classification:
- *Botanic.*—*Dianthus caryophyllus.*
- *Commercial.*—Spray carnation.

Form: Bush of tall spray shape.
Height: Approximately one meter.
Growth rate: Rapid, upright, sturdy and strong.
Branching: Alternate.
Foliage: Of medium quantity.
- *Size of leaf.*—About 13 cm. long.
- *Form of leaf.*—Sessile and lanceolated with acute tip and smooth margins.

- *Texture.*—Leathery.
- *Color.*—Upper Side — Blue Green. Under Side — Blue Green.
- *Leaflets.*—None.

THE BUD

Size: Medium.
- *Diameter.*—About 12 to 15 mm.
- *Length.*—About 2 to 3 mm.

Form: Generally cylindrical and of inverted oval shape.
Rate of opening: With mature bud, the flowers will appear about three days later.
Color: When sepals first divide and when petals begin to unfurl, the petal colors are red.
Sepals: The sepals are hooded over the bud before dividing and stand up as the flower petals unfurl.
- *Shape.*—Generally ovate with somewhat acuminate tip.
- *Color.*—Inside — Light Green. Outside — Dark Green.

Calyx:
- *Size.*—Medium.
- *Shape.*—Funnel-shaped.
- *Aspect.*—Smooth.
- *Splitting.*—The calyx does not split.

Flower stem:
- *Length.*—About 45 to 50 cm.
- *Character.*—Rigid and erect.
- *Color.*—Dark Green.

THE FLOWER

Blooming habit: Continuous and profuse.
Size of bloom: Small.
- *Diameter.*—About 50 to 55 mm.
- *Depth.*—About 35 to 40 mm.

Borne: As cluster with more than three flowers per stem.
Shape: With high center when bloom first opens; and as the bloom matures, it tends to flatten.
Petalage:
- *Number of petals.*—30.
- *Arrangement.*—Imbricated.
- *Form.*—Folded with closely dentated margin.
- *Color.*—Outer Petal — 45B-C. Inside Petal — 45B-C.
- *Texture.*—Soft.
- *Appearance.*—Velvety.

Petaloids: About 30 in number and about 4 cm. long.

*Color.*—Same as petals.

Flower stem: Up to 50 cm. long.

*Color.*—Blue Green.

*Character.*—Sturdy and upright.

Persistence: Petals hang on and dry.

Fragrance: Weak.

Lasting quality: As a cut flower — 10 to 16 days.

REPRODUCTIVE ORGANS

Stamens:

*Anthers.*—Many in number, evenly arranged and 3 to 4 mm. long. Color: Straw Yellow.

*Filaments.*—Length: Varies from 10 to 30 mm. Color: White with greenish base.

*Pollen.*—Color — Pink.

Pistils:

*Number.*—Not more than three.

*Styles.*—Length: About 35 mm. Color: Cream, with red shaded ventral side.

*Stigmas.*—Color: Pink to rose.

Ovaries: Normal, light green in color with yellowish top.

This new carnation variety most nearly resembles the variety "Red Baron"; however, it is taller, of a bushier growth and the flower petals are more serrated.

I claim:

1. The new and distinct variety of spray carnation, substantially as herein shown and described, characterized by its continuous and profuse flower production, its rapid growth rate, and its normal height of about one meter with flower stems of about 45 to 50 centimeters in length.

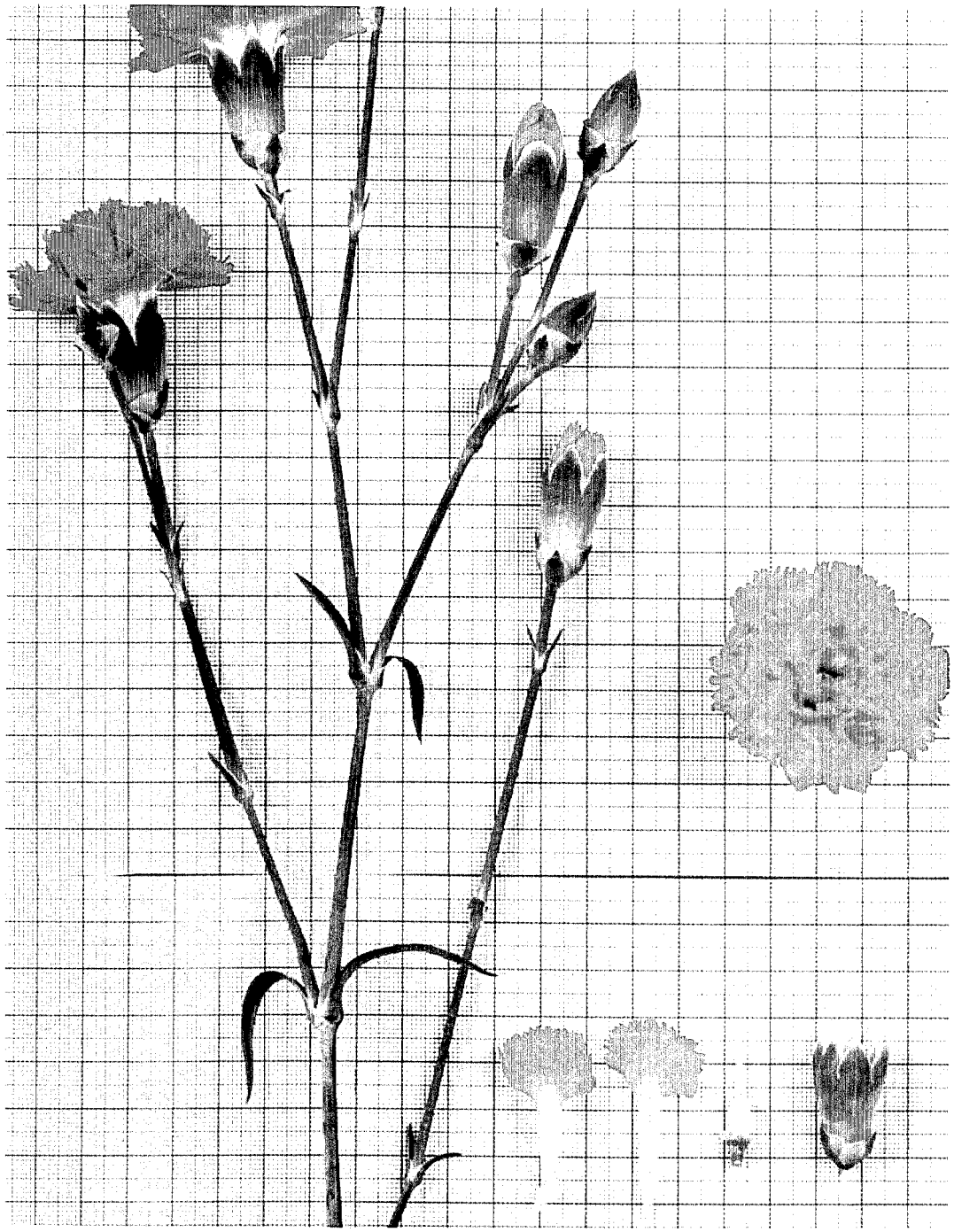

* * * * *